United States Patent
Tokunaga et al.

(10) Patent No.: US 8,289,810 B2
(45) Date of Patent: Oct. 16, 2012

(54) WINDING STATE EVALUATION METHOD FOR TAPE FILM AND WINDING METHOD FOR TAPE FILM

(75) Inventors: Hisatsugu Tokunaga, Isesaki (JP); Masanori Higano, Isesaki (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 317 days.

(21) Appl. No.: 12/680,805

(22) PCT Filed: Mar. 19, 2008

(86) PCT No.: PCT/JP2008/055094
§ 371 (c)(1),
(2), (4) Date: Mar. 30, 2010

(87) PCT Pub. No.: WO2009/044565
PCT Pub. Date: Apr. 9, 2009

(65) Prior Publication Data
US 2010/0209688 A1 Aug. 19, 2010

(30) Foreign Application Priority Data
Oct. 1, 2007 (JP) .................................. 2007-257664

(51) Int. Cl.
*B32B 38/18* (2006.01)
*G01N 29/00* (2006.01)
*B65H 26/00* (2006.01)

(52) U.S. Cl. ............................................ 367/87; 367/96
(58) Field of Classification Search ................... 367/96, 367/87; 153/361; 73/599; 428/220
See application file for complete search history.

(56) References Cited

U.S. PATENT DOCUMENTS
2010/0209688 A1* 8/2010 Tokunaga et al. ............. 156/361

FOREIGN PATENT DOCUMENTS
| JP | 5 280967 | 10/1993 |
| JP | 8 189923 | 7/1996 |
| JP | 2002 274707 | 9/2002 |
| JP | 2005 206301 | 8/2005 |
| JP | 2006 225135 | 8/2006 |
| JP | 2007 213726 | 8/2007 |
| WO | WO 2009044565 A1 * | 4/2009 |

* cited by examiner

*Primary Examiner* — Daniel Pihulic
(74) *Attorney, Agent, or Firm* — Oblon, Spivak, McClelland, Maier & Neustadt, L.L.P.

(57) ABSTRACT

A winding state evaluation method of a tape film includes a step of determining the attenuation rate of ultrasonic wave for the tape film (2) by sending an ultrasonic wave to the tape film (2) in parallel with the direction of the axis of rotation of a core (1) and receiving its reflected wave or transmitted wave, and a step of evaluating the winding state of the tape film (2) from the distribution state of the attenuation rate in the tape film (2). The method can judge the winding state of the tape film objectively by presenting its numerical representation concretely without relying upon sensual evaluation.

8 Claims, 1 Drawing Sheet

[FIG. 1]
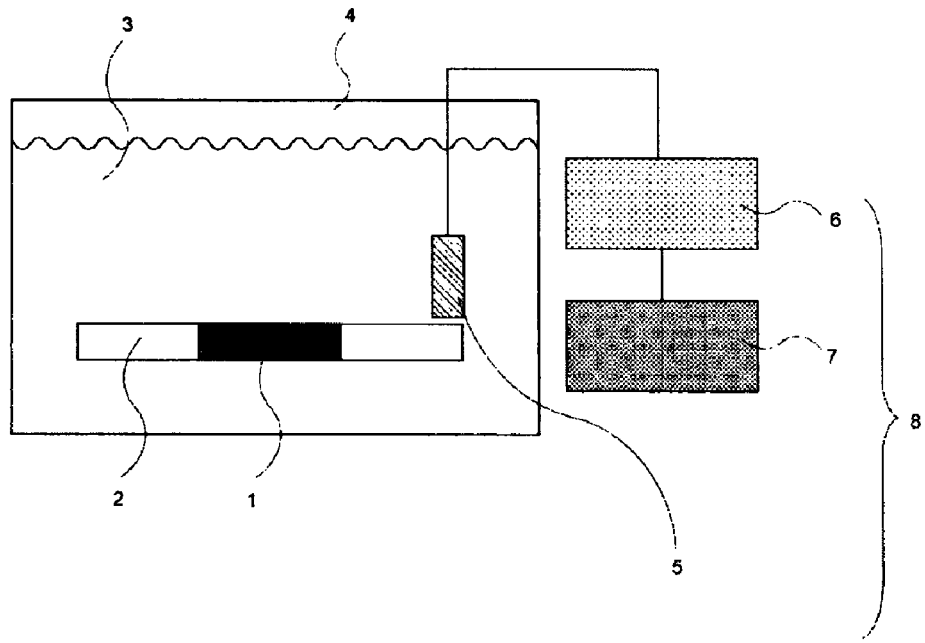
[FIG. 2]
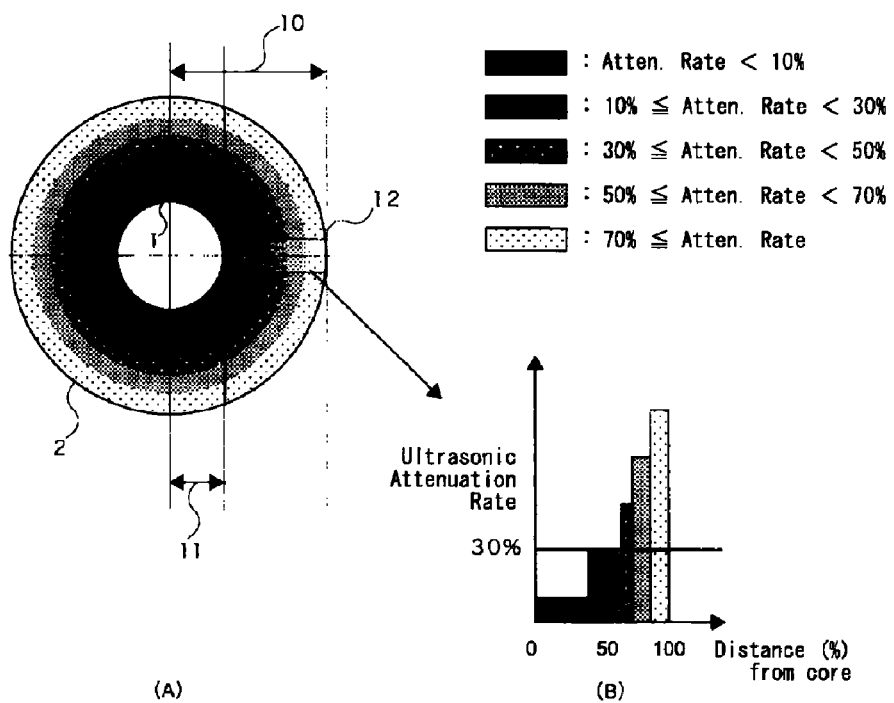

WINDING STATE EVALUATION METHOD FOR TAPE FILM AND WINDING METHOD FOR TAPE FILM

TECHNICAL FIELD

This application is a 371 of PCT/JP08/55094, filed Mar. 19, 2008.

The present invention relates to a winding state evaluation method, a winding method for tape film in which the winding conditions are controlled based on the results of the aforementioned evaluation method, and a tape film wound using the aforementioned winding method. Examples of tape films include tape films that are slit to a narrow width, such as a cover tape for carrier tape used when transporting electronic components.

BACKGROUND ART

When transporting chip-type electronic components such as IC's, carrier tape formed by embossing plastic sheets to consecutively form recesses at standard intervals is generally used. After inserting chip-type electronic components into these recesses, the electronic components are sealed by heat-sealing the top surface of the carrier tape with a cover tape, then they are wound onto cores for transport.

The cover tape used for sealing is normally slit into the form of a narrow tape film from a wide original roll, then wound onto a core to go to market.

However, if the tape film is poorly wound, then ambient temperatures and humidity during transportation or storage can cause the winding to become deformed, and in extreme cases, result in unwinding, making it impossible to use.

Possible causes of poor windings include problems with the tape film itself, such as the thickness of the tape film being uneven (presence of thickness variations), and problems with the winding method such as having inappropriate tension settings during the winding process.

Examples of means for improving the method of winding tape film include a method wherein the rotational torque of the winding motor is made variable during the process of winding the tape film onto a core, so that it can be continuously wound while changing the force of tension (Patent Document 1), a method of using a touch roller during the winding process, such as to move the support portion of the touch roller in accordance with the winding diameter (Patent Document 2), and a method of using a press roller during the winding process, so as to control the pressure load when beginning the winding process and at the end of the winding process (Patent Document 3).

Patent Document 1: JP2002-274707A
Patent Document 2: JP2005-206301A
Patent Document 3: JP2006-225135A

DISCLOSURE OF THE INVENTION

Problems to be Solved by the Invention

However, the determination of whether or not a tape film is appropriately wound must depend on indefinite methods based on sensory evaluation, such as by a highly experienced worker making visual observations or by direct manual contact to find the state of the edge surfaces of the tape film wound onto a core.

Additionally, even when wound into a state judged to be free of problems by visual observation and touch, there are cases in which the tape film can become loose and unwound during transportation or storage.

Therefore, there was a demand for effective means of objectively and quantitatively determining whether or not the winding state of a tape film wound onto a core is good, without depending on subjective evaluations based on vision and touch.

The present invention was made in consideration of the above-described circumstances, and offers a method of evaluating the winding state of a tape film enabling the winding state of a tape film wound onto a core to be objectively and precisely determined, a tape film winding method enabling deformations of the winding state and unwinding to be prevented from occurring during transport and storage by controlling the winding conditions based on evaluation results based on the aforementioned evaluation method, and a tape film wound using the aforementioned winding method.

Means for Solving the Problems

As a result of diligent research toward a method accomplishing the above-described object, the present inventors discovered that an objective determination of whether or not the winding state is good can be made by generating ultrasonic waves toward a tape film wound onto a core, in a direction parallel to the axis of rotation of the core, receiving the reflected or transmitted waves to thereby determine the attenuation rate of ultrasonic waves due to the tape film, and analyzing the distribution of the attenuation rate in the tape film.

That is, the present invention offers a method of evaluating the winding state of a tape film wound onto a core, the method being characterized by comprising a step of generating ultrasonic waves toward the tape film, in a direction parallel to an axis of rotation of the core, and receiving the reflected or transmitted waves, to determine a rate of attenuation of the ultrasonic waves in the tape film; and a step of evaluating the winding state of the tape film based on the distribution of the rate of attenuation in the tape film.

According to this method of evaluating the winding state of a tape film, it is possible to objectively and quantitatively determine whether or not the winding state of a tape film wound onto a core is good, without depending on the senses of vision or touch.

Additionally, by controlling the winding conditions based on the obtained evaluation results, a method of winding a tape film providing a good winding state and a tape film with a good winding state can be offered.

Effects of the Invention

The present invention enables a highly precise and objective determination of whether or not the winding state of a tape film wound onto a core is good. Additionally, since the results of the evaluation method can be used to optimize the winding conditions, the invention also offers a method of winding a tape film with a good winding state and a tape film with a good winding state.

BRIEF DESCRIPTION OF THE DRAWINGS

FIG. 1 A schematic view of a measuring method of an ultrasonic flaw detecting device as described by the present invention.

FIG. 2 A schematic view of a method of deriving a rate of attenuation of an ultrasonic wave from measurements.
1 core
2 tape film
3 water
4 measuring water tank
5 probe
6 ultrasonic flaw detecting device
7 computer
8 ultrasonic attenuation rate measuring system
9 radius of tape film
10 radius of core
11 evaluation range

BEST MODES FOR CARRYING OUT THE INVENTION

Herebelow, an embodiment of the present invention will be explained using the drawings. In all of the drawings, the same structural elements will be assigned the same reference numbers, and their explanations will be omitted.

<Summary of Method of Evaluating Winding State of Tape Film>

FIG. 1 is a conceptual diagram explaining the method of evaluating the winding state of the tape film of the present embodiment.

The method of evaluating the winding state of a tape film according to the present embodiment, as shown in FIG. 1, is performed by immersing a tape film 2 wound onto a core 1 in a measuring water tank 4 filled with water 3, and using an ultrasonic attenuation rate measuring system 8 comprising an ultrasonic probe 5, an ultrasonic flaw detecting device 6 connected to the ultrasonic probe 5, and a computer 7 for processing and displaying position data of the ultrasonic probe 5 and ultrasonic attenuation rate data outputted by the ultrasonic flaw detecting device 6.

<Tape Film>

The tape film 2 is formed by molding a resin generally used for industrial purposes into a thin film and slitting to a narrow width. Examples of such resins include polyesters such as polyethylene terephthalate (PET), polyethylene naphthalate (PEN), and mixtures of polyethylene terephthalate and polyethylene naphthalate, polyolefins such as polypropylene and polyethylene, polyvinyl chloride resins and styrene resins.

The tape film 2 may be a film of single layer structure composed of the above-described resin, or a film of multilayer structure formed by using the aforementioned film as a substrate, then laminating and integrating sealing layers composed of olefin resins, styrene resins or mixtures thereof onto such a substrate.

While the thickness of the tape film 2 is not particularly limited, it should be at least 0.03 mm and at most 2 mm, preferably 0.1 mm or less, and more preferably 0.08 mm or less. A thickness of at least 0.03 mm is preferable because this makes it less likely for trouble such as tape tearing to occur when winding a tape film 2 onto a core 1 or when pulling out the tape film 2 from a wound state. On the other hand, the thickness of the tape film 2 should be at most 2 mm for ease of handling and in view of the major applications.

While the width of the tape film 2 is not particularly limited, it should generally be at least 1 mm and at most 50 mm, preferably 10 mm or less. The width should preferably be at least 1 mm to make it less likely for unwinding to occur during transport or storage. On the other hand, the width of the tape film 2 should be 50 mm or less for ease of handling during use and in view of the major applications.

As for the method of slitting the tape film 2, a shear cutting method of slitting a film between a lower blade and an upper blade is suitable for use, but the invention is not limited thereto, and various slitting methods can be used.

<Core>

As the core 1, it is suitable to use one composed of a paper material or plastic material. A plastic material is preferably used for the ability to withstand stress exerted on the core 1 when winding the tape film 2. Additionally, a resin incorporating glass fibers may be used as the material for the purpose of improving the strength of the core 1.

<Ultrasonic Attenuation Rate Measuring System>

The ultrasonic attenuation rate measuring system 8 may be any system that is normally used in non-destructive inspection, and is not limited to the system shown in the present embodiment.

The ultrasonic attenuation rate measuring system 8 shown in FIG. 1 comprises an ultrasonic probe 5, an ultrasonic flaw detecting device 6 connected to this ultrasonic probe 5, and a computer 7 connected thereto.

The ultrasonic attenuation rate measuring system 8 shown in FIG. 1 is a single-probe method in which a single probe 5 generates ultrasonic pulses and receives reflected ultrasonic pulses. The present invention may use not only a single-probe method but also a two-probe method in which ultrasonic pulses are separately generated and received. In the case of a two-probe method, either a pulse reflection method or a pulse transmission method may be used.

The ultrasonic attenuation rate measuring system 8 shown in FIG. 1 makes use of a water-immersion flaw detecting method in which a sample is immersed in water 3. In other words, the ultrasonic attenuation rate measuring system 8 shown in FIG. 1 measures the ultrasonic attenuation rate by immersing a tape film 2 in water 3 filling a measuring water tank 4, generating an ultrasonic pulse toward the tape film 2 immersed in the water and receiving the reflected wave, using a single probe 5. Aside from water 3, the medium filling the measuring water tank 4 may be a grease such as is normally used in ultrasonic flaw detection.

The probe 5 generates an ultrasonic pulse toward the tape film 2 which is the sample, in a direction parallel to the direction of the rotational axis of the core 1, and receives the reflected ultrasonic pulse. Here, the expression "parallel" refers to a direction roughly parallel to the axis of rotation, and there is no need for it to be perfectly parallel. Therefore, measurements are possible as long as the pulse is, for example, within the range of an angle of inclination of about ±10° with respect to the axis of rotation. The position of the probe 5 can be controlled by the ultrasonic flaw detecting device 6 or the computer 7, and the position information of the probe 5 can always be seen on the computer 7.

The control of the ultrasonic pulses generated by the probe 5 and the processing of the received ultrasonic pulses are performed by the ultrasonic flaw detecting device 6. The ultrasonic flaw detecting device 6 computes the ultrasonic attenuation rate based on the ultrasonic pulse generated by the probe 5 and the ultrasonic pulse received by the probe 5, and sends the computation results to the computer 7.

The computer 7 processes the position information of the probe 5 in association with the ultrasonic attenuation rate data received from the ultrasonic flaw detecting device 6, and displays the distribution of the ultrasonic attenuation rate on the tape film 2.

<Measuring Method of Ultrasonic Attenuation Rate>

The method of measuring the ultrasonic attenuation rate of the tape film 2 wound onto the core 1 may be any generally used method, and is not particularly limited. Here, a measuring method using the ultrasonic attenuation rate measuring system 8 shown in FIG. 1 shall be explained.

The measuring water tank 4 is filled with water 3, then the tape film 2 which is the sample is completely immersed in the measuring water tank 4. Since any air left in the boundary between the tape film 2 and the water 3 will generate noise, it should be completely removed.

The measurement of the ultrasonic attenuation rate is performed by generating an ultrasonic pulse from the probe 5 toward the tape film 2 which is wound onto a core 1 in a direction parallel to the axis of rotation of the core 1, then receiving the reflected wave at the probe 5.

The ultrasonic attenuation rate is computed based on the difference between the intensity of the generated ultrasonic pulse and the intensity of the received ultrasonic pulse, making use of the fact that the ultrasonic pulses generated by the probe 5 will be attenuated by acoustic attenuation portions in the sample tape film 2, typically due to the presence of air trapped during the winding process.

Since the rate of attenuation will generally vary depending on the distance from the core 1, in a concentric distribution centered at the core 1, by simply scanning the probe 5 linearly in only a radial direction of the tape film 2 to study the local ultrasonic attenuation rate distribution conditions, it is possible to make roughly the same evaluation as when the tape film 2 is measured over its entire range. Therefore, when the ultrasonic attenuation rate needs to be quickly and easily measured, it is sufficient to measure the tape film 2 in only a radial direction. However, since there are anomalous cases of localized air pockets, it is preferable to scan the probe 5 over the entirety of the tape film 2 and measure the distribution condition of the ultrasonic attenuation rate over the entire range of the tape film 2 in order to make an accurate evaluation of the winding state.

Next, the computer 7 processes the position information of the probe 5 in association with the ultrasonic attenuation rate data at that position, and displays the ultrasonic attenuation rate distribution of the tape film 2.

<Tape film Winding State Evaluating Method>

The method of evaluating the winding state of the tape film is performed, for example, as shown in FIG. 2.

FIG. 2(A) shows the distribution of the ultrasonic attenuation rate over the entire range of the tape film 2 wound onto the core 1. In this drawing, the ultrasonic attenuation rate is divided into the five stages of 1) less than 10%, 2) greater than or equal to 10% and less than 30%, 3) greater than or equal to 30% and less than 50%, 4) greater than or equal to 50% and less than 7%, and 5) greater than or equal to 70%, so as to enable the distribution of the ultrasonic attenuation rate to be visually grasped. The ultrasonic attenuation rate distribution can be more precisely grasped by making the width of each division narrower as needed. Additionally, it is also preferable to add color gradations, patterns or contour lines to make the variation in the ultrasonic attenuation more easily visible.

As shown in this drawing, the ultrasonic attenuation rate is typically distributed concentrically about the core 1. However, there are rare cases in which local acoustic attenuation portions, in other words, local air pockets, are formed regardless of the winding conditions. Such locally occurring winding anomalies can be found by analyzing the distribution of the ultrasonic attenuation rate over the entire range of the tape film 2.

FIG. 2(B) is a graph showing the distribution of the ultrasonic attenuation rate with respect to the distance from the core 1 in a radial direction (evaluation range 12) of the tape film 2. Here, the distance from the core 1 is represented by the proportion (%) with respect to the length of the radius 11 of the core 1 subtracted from the radius 10 of the tape film 2 wound onto the core 1.

One cause of winding problems such as unwinding of the tape film 2 is that the area exhibiting a certain ultrasonic attenuation rate is not large enough to reach the proportion that must be covered in the radial direction of the tape film 2. The present invention is based on the discovery that winding problems such as unwinding will not occur if the ultrasonic attenuation rate is 30%, or less over a range of at least 50% of the length of the radius 11 of the core 1 subtracted from the radius 10 of the tape film 2 wound onto the core 1. However, since the winding state is affected by transportation and storage conditions of the tape film 2, the above value should preferably be revised as needed.

<Tape Film Winding Method>

A method of winding a tape film that does not cause winding problems such as unwinding can be offered by adjusting the various winding conditions based on the results of the above-described evaluation of the winding state of the tape film.

A typical example of a winding condition that should be considered is the winding tension applied to the tape film during the winding process. Additionally, in winding formats wherein a tape film 2 is pressed against the core 1 by a touch roller or press roller, the pressure applied by the tape film 2 should also be considered.

As for the method of winding the tape film 2 onto the core 1, a format capable of simultaneously winding tape films 2 simultaneously slit into a plurality of ribbons onto a plurality of winding shafts bearing cores 1 is preferable. In this format, the winding shafts should be friction-controlled so as to enable the winding tension on each tape film 2 to be separately controlled.

The winding tension is set so as to be able to achieve an ultrasonic attenuation rate distribution in which winding problems such as unwinding of the tape film 2 will not occur, in consideration of the results of evaluation of the winding state. Typically, the winding tension is set so that the ultrasonic attenuation rate is 30% or less over a range of at least 50% of the length of the radius 11 of the core 1 subtracted from the radius 10 of the tape film 2 wound onto the core 1.

The winding conditions may be set in any manner, whether in a manner varying at a constant gradient from the beginning of the winding, or in a manner appropriately adjusted depending on the winding radius, as long as it is capable of achieving an ultrasonic attenuation rate distribution in which winding problems such as unwinding will not occur.

Additionally, if the tape film 2 is pressed against the core 1 by a press roller or the like when winding the tape film 2 onto the core 1, the pressure should be set so as to be able to achieve an ultrasonic attenuation rate distribution which will not result in winding problems such as unwinding of the tape film 2, in consideration of the evaluation results of the winding state. Typically, the pressure is set so that the ultrasonic attenuation rate is 30% or less over a range of at least 50% of the length of the radius 11 of the core 1 subtracted from the radius 10 of the tape film 2 wound onto the core 1.

The pressure conditions may be set in any manner, whether in a manner wherein the pressure is kept constant from the beginning of the winding, or in a manner appropriately adjusted depending on the winding radius, as long as it is capable of achieving an ultrasonic attenuation rate distribution in which winding problems such as unwinding will not occur.

<Functions and Effects>

Herebelow, the functions and effects of the method of evaluating the winding state of the tape film of the present embodiment will be explained with reference to FIG. 1 and FIG. 2.

The method of evaluating the winding state of a tape film according to the present embodiment comprises a step of generating ultrasonic waves toward a tape film, in a direction parallel to an axis of rotation of the core, and receiving the reflected or transmitted waves, to determine a rate of attenuation of the ultrasonic waves in the tape film 2; and a step of evaluating the winding state of the tape film 2 based on the distribution of the rate of attenuation in the tape film 2.

Due to this structure, it is possible to objectively determine, in a quantified manner, whether or not the winding state of a tape film 2 wound onto a core is good, without depending on the senses of vision or touch.

Additionally, the attenuation rate distribution is preferably a distribution in the radial direction of the tape film 2 wound onto the core.

In this case, since the ultrasonic attenuation rate is distributed roughly concentrically about the core 1, an evaluation roughly equivalent to making measurements over the entire range of the tape film 2 can be achieved by simply studying the distribution of the ultrasonic attenuation rate linearly in the radial direction of the tape film 2, thus enabling quick and convenient evaluation.

Additionally, a method of winding a tape film 2 with the winding conditions controlled based on the results of the evaluation by the above evaluation method can be achieved. In particular, it is preferable to control the winding conditions so that the ultrasonic attenuation rate is 30% or less over a range of at least 50% of the length of the radius 11 of the core 1 subtracted from the radius 10 of the tape film 2 wound onto the core 1.

According to this winding method, the tape film 2 can be wound in such a manner that winding anomalies such as unwinding during transport and storage will not occur.

Additionally, the tape film 2 should have a width of at least 1 mm and at most 50 mm. In this case, trouble such as tape tearing is not likely to occur, and the tape film is easy to handle.

Furthermore, it is preferable for the thickness of the tape film 2 to be at least 0.03 mm and at most 2 mm.

In this case, unwinding is not likely to occur during transportation or storage, and the tape film is easy to handle.

Additionally, the winding method can be particularly favorably used if the tape film 2 is a multi-layer film.

In general, multi-layer films are formed by sequentially laminating plural kinds of resin films, so it is difficult to make the thickness of the film uniform and air pockets that are the cause of unwinding and the like are more likely to occur than in films with a single-layer structure. According to this winding method, even a multi-layer film that has minor variations in thickness and is susceptible to winding anomalies can be wound without resulting in problems such as unwinding, by quantifying and precisely evaluating the state of winding, and setting the optimum winding conditions based on the results of the evaluations.

Additionally, as the multi-layer film type tape film 2, a cover tape for carrier tape can be especially be used.

While cover tapes for carrier tape can be rendered unusable by winding anomalies such as unwinding, such problems can be prevented by using the above-described winding method.

Additionally, the wound tape film can be favorably used as a result of the above-described tape film winding method.

With this tape film, the rate of occurrence of winding anomalies such as unwinding during transportation and storage is low.

While embodiments of the present invention have been described above with reference to the drawings, these are simply examples of the present invention, and various structures aside from the above are possible.

For example, while the above-described embodiments use a water-immersion type flaw detecting method using a single probe, a two-probe method in which ultrasonic pulses are separately generated and received can also be used, and a direct contact method in which the sample is not immersed in water is also possible. No matter which type of method is used, the ultrasonic attenuation rate can be measured in the same manner as in the above-described embodiments, so similar functions and effects can be achieved.

EXAMPLES

Herebelow, the present invention will be further explained with reference to examples, but the present invention is not limited thereto.

<Measurement of Ultrasonic Attenuation Rate>

The ultrasonic attenuation rate was measured using an ultrasonic flaw detecting device SDS5500 (ultrasonic flaw detector HIS3HF) manufactured by Krautkramer Japan and an ultrasonic attenuation rate measuring system equipped with a Φ12.7 mm probe. A measuring water tank was filled with water, a tape film wound onto a core was completely immersed therein, and a probe was scanned in a radial direction of the tape film to study the distribution of the ultrasonic attenuation rate.

The tape film was wound so as to make the regions in which the ultrasonic attenuation rate is 30% or less satisfy the proportions indicated below.

Example 1

A tape film was cut to a width of about 5 mm from an original roll having a width of 440 mm formed by laminating a 16 μm thick substrate of polyethylene terephthalate with a 38 μm thick polyethylene resin layer and a 8 μm thick styrene resin layer, then wound onto a core of radius 46.5 mm at a winding rate of 50 m/min. When winding the tape film, the winding tension was adjusted so as to raise the settings in the range of 50 gf to 70 gf from the beginning to the end of the winding process, resulting in a tape film wound so that the range where the ultrasonic attenuation rate was 30% or less occupied 69%.

Example 2

Same as Example 1, aside from the fact that the winding tension on the tape film during winding was adjusted in the range of 40 gf to 65 gf, resulting in a tape film wound so that the range where the ultrasonic attenuation rate was 30% or less occupied 50%.

Example 3

Same as Example 1, aside from the fact that a tape film 2 with a width of about 9 mm was used, and the winding tension on the tape film during winding was adjusted within the range of 130 gf to 160 gf, resulting in a tape film wound so that the range where the ultrasonic attenuation rate was 30% or less occupied 60%.

Comparative Example 1

Same as Example 1, aside from the fact that the winding tension on the tape film during winding was adjusted so as to lower the setting within the range of 55 gf to 70 gf from the beginning to the end of the winding process, resulting in a tape film wound so that the range where the ultrasonic attenuation rate was 30% or less occupied 25%.

Comparative Example 2

Same as Example 1, aside from the fact that the winding tension on the tape film during winding was adjusted in the range of 10 gf to 20 gf, resulting in a tape film wound so that the range where the ultrasonic attenuation rate was 30% or less occupied 0%.

<Evaluation of Winding State>

Next, the winding states of the tape films wound as indicated above were evaluated visually.

The evaluations of the winding states of the tape films were performed after leaving the tape films in high-temperature or low-temperature environments, to simulate various transportation and storage environments.

High-Temperature Environment Test

A tape film wound onto a core was placed in a box composed of cardboard approximately 7 mm thick, with inner dimensions of length about 220 mm×width about 220 mm×height about 180 mm, which was left in an oven set to 60° C. for 2 hours. After removing the box from the oven, it was left for at least 24 hours in an environment of temperature 23° C. and 50% humidity, after which the tape film was removed from the box and its winding state evaluated by eye.

Low-Temperature Environment Test

A tape film was left in an exposed state for 1 hour in a refrigerator set to 15° C., and the state of winding was evaluated by eye inside the refrigerator.

The results of the evaluation of the winding state are shown in the following Table 1.

TABLE 1

| | Slit Width | Range (%) ultrasonic attenuation | Winding State Evaluation | |
|---|---|---|---|---|
| | (mm) | 30% or less | High Temp | Low Temp |
| Example 1 | about 5 mm | 69% | ○ | ○ |
| Example 2 | about 5 mm | 50% | ○ | ○ |
| Example 3 | about 9 mm | 60% | ○ | ○ |
| Comparative Example 1 | about 5 mm | 25% | X | X |
| Comparative Example 2 | about 5 mm | 0% | X | X |

In Table 1, the symbols have the following meanings.
○ (good): No loosening or unwinding observed by eye.
X (poor): Loosening or unwinding observed by eye.

<Analysis of Tests>

As is clear from Table 1, there is a certain correlation between the winding state and the ultrasonic attenuation rate, and based on this relationship, the winding state of a tape film, which has conventionally been dependent on the human senses, can be quantified to enable objective and precise evaluations. Specifically, winding anomalies such as unwinding do not occur if the ultrasonic attenuation rate is 30% or less over a range of at least 50% of the length of the radius of the core subtracted from the radius of the tape film wound onto the core.

The present invention has been described above with reference to the examples. These are merely examples, and those skilled in the art will recognize that various modifications are possible, and such modifications may also fall within the scope of the present invention.

INDUSTRIAL APPLICABILITY

The method of evaluating a tape film according to the present invention enables specific quantification and objective determination that does not depend on indefinite methods of sensory evaluation based on the experiences of skilled workers, and thus can be used to advantage in cover tapes for carrier tapes requiring highly precise evaluations of the winding state. Similarly, since the method of winding a tape film by controlling the winding conditions based on the results of said evaluation is capable of suppressing the occurrence of winding anomalies such as unwinding during transportation and storage, it can be used to advantage, particularly in cover tapes for carrier tape.

The invention claimed is:

1. A method of evaluating the winding state of a tape film wound onto a core, the method comprising:
   generating ultrasonic waves toward the tape film, in a direction parallel to an axis of rotation of the core, and receiving the reflected or transmitted waves, to determine a rate of attenuation of the ultrasonic waves in the tape film; and
   evaluating the winding state of the tape film based on a distribution of the rate of attenuation in the tape film.

2. A method of evaluating the winding state of a tape film in accordance with claim 1, wherein said distribution of the rate of attenuation is a distribution in a radial direction of the tape film wound onto a core.

3. A method of winding a tape film, comprising controlling the winding conditions of the tape film onto a core based on evaluation results of a method of evaluation of the winding state of a tape film wound onto a core, said method of evaluation of the winding state of a tape film wound onto a core comprising:
   generating ultrasonic waves toward the tape film, in a direction parallel to an axis of rotation of the core, and receiving the reflected or transmitted waves, to determine a rate of attenuation of the ultrasonic waves in the tape film; and
   evaluating the winding state of the tape film based on a distribution of the rate of attenuation in the tape film.

4. A method of winding a tape film in accordance with claim 3, wherein said winding conditions are controlled so that the ultrasonic attenuation rate is 30% or less over a range of at least 50% of the length of the radius of the core subtracted from the radius of the tape film wound onto the core.

5. A method of winding a tape film in accordance with claim 3, wherein the width of said tape film is at least 1 mm, and at most 50 mm.

6. A method of winding a tape film in accordance with claim 3, wherein the thickness of said tape film is at least 0.03 mm, and at most 2 mm.

7. A method of winding a tape film in accordance with claim 3, wherein said tape film is a multi-layer film.

8. A method of winding a tape film in accordance with claim 7, wherein said tape film is a cover tape for a carrier tape.

* * * * *